United States Patent [19]

Modin

[11] Patent Number: 4,705,052
[45] Date of Patent: Nov. 10, 1987

[54] HAIRSTYLING BRUSH AND A METHOD FOR HANDLING HAIRSTYLING BRUSHES

[76] Inventor: Jimmie D. Modin, 728 S. 10th, Salina, Kans. 67401

[21] Appl. No.: 861,841

[22] Filed: May 12, 1986

Related U.S. Application Data

[63] Continuation-in-part of Ser. No. 648,474, Sep. 10, 1984, Pat. No. 4,605,023.

[51] Int. Cl.$^4$ ............................................. A45D 44/18
[52] U.S. Cl. ...................................................... 132/85
[58] Field of Search .......................... 132/85; 422/120; 15/176, 165, 144 B

[56] References Cited

U.S. PATENT DOCUMENTS

| | | | |
|---|---|---|---|
| 3,072,938 | 1/1963 | Phaneof | 15/176 |
| 3,128,487 | 4/1964 | Vellis | 15/176 |
| 4,486,915 | 12/1984 | Steward et al. | 132/85 |

Primary Examiner—Robert Peshock
Attorney, Agent, or Firm—John Wade Carpenter

[57] ABSTRACT

A method for handling hairstyling brushes comprising the steps releasing a boss from within an aperture of a biasing latch and from extending and operating through a slot of a generally cylindrical handle in order to separate the brush from the cylindrical handle, and positioning the brush in a sterilizing fluid contained in a reservoir container of an apparatus for handling hairstyling brushes which includes a pair of end walls, a back wall secured to the end walls, a bottom attached to the end walls and the back wall, an upright support wall connected to the bottom and to the back wall. The apparatus for handling hairstyling brushes additionally includes a cross brace attached to the support wall and to one of the end walls, an upper door pivotally attached to the cross brace, a lower door pivotally connected to the bottom underneath the upper door, and a perforate tray slidably positioned to the upright support wall and to one of the end walls behind the upper door.

6 Claims, 13 Drawing Figures

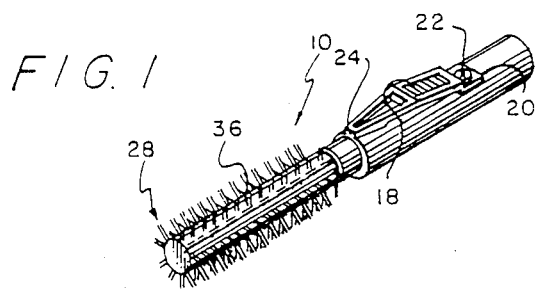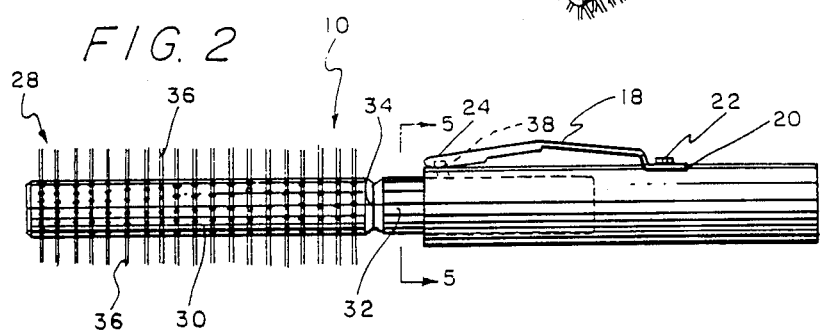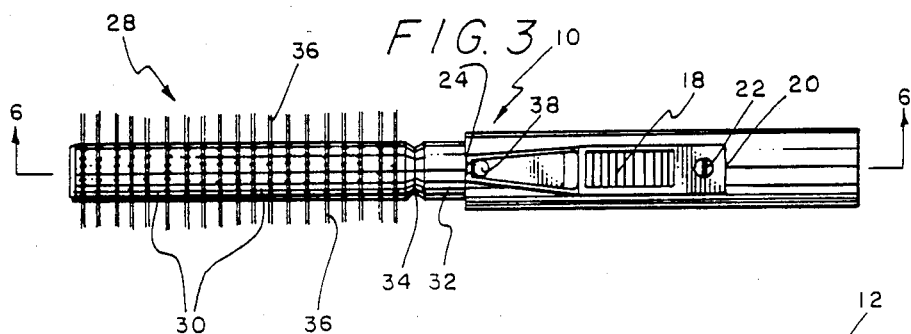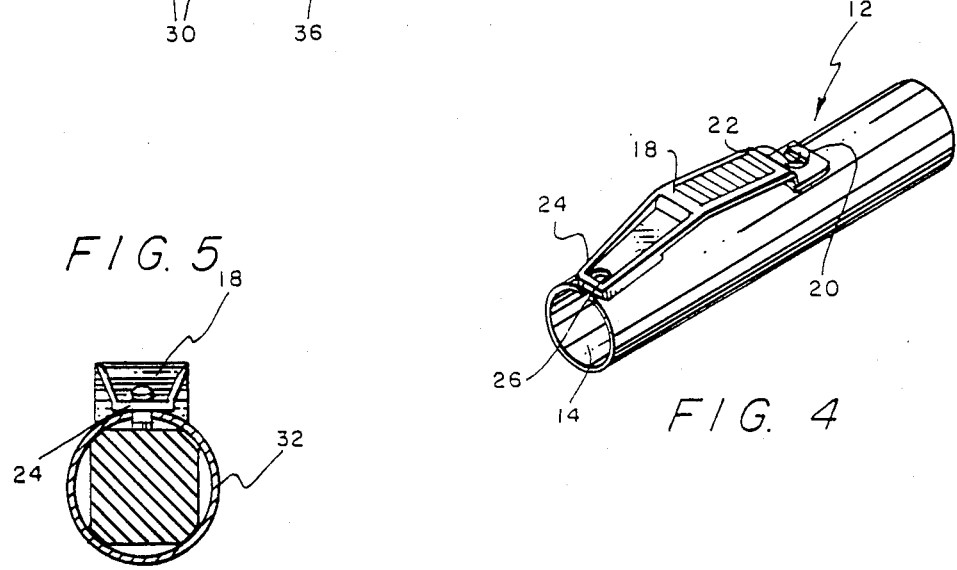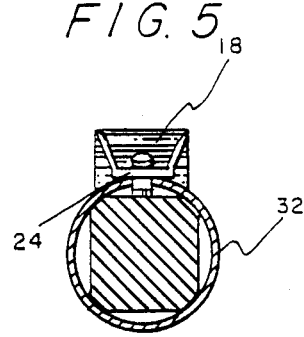

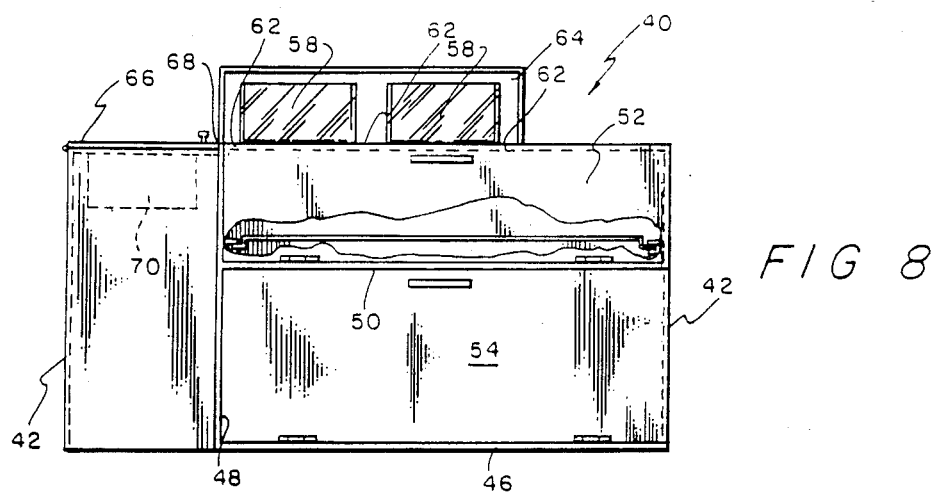
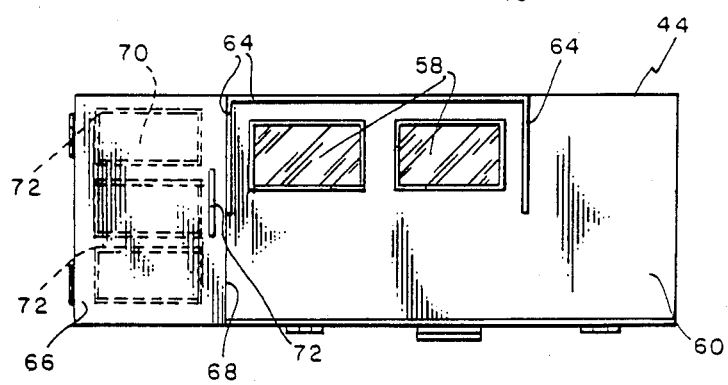
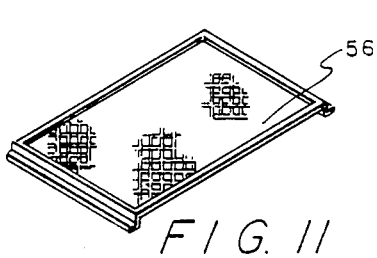
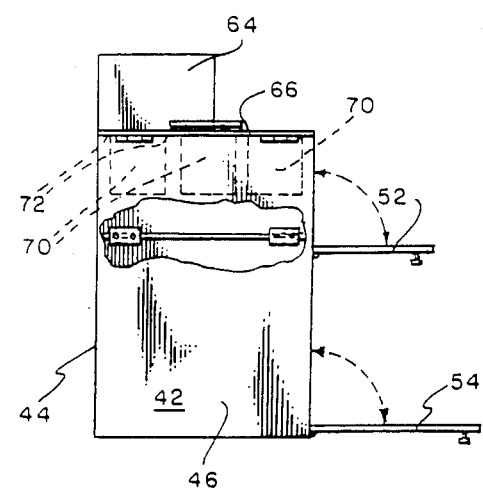
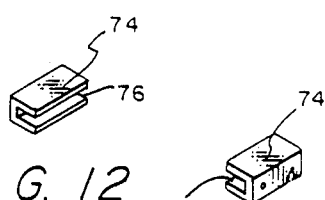
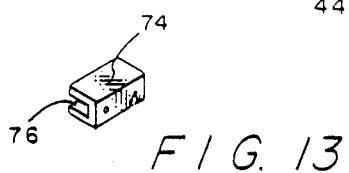

HAIRSTYLING BRUSH AND A METHOD FOR HANDLING HAIRSTYLING BRUSHES

This a continuation-in-part application of my copending patent application having Ser. No. 648,474, and filed Sept. 10, 1984, now U.S. Pat. No. 4,605,023, issued Aug. 12, 1986.

BACKGROUND OF THE INVENTION

1. Field of the Invention

This invention provides an apparatus for handling hairstyling brushes, and a method for handling hairstyling brushes.

2. Description of the Prior Art

U.S. Pat. No. 1,992 by Lewis teaches a brush having an opening in the handle of the brush, and the brush shank having a spring member extendable into the opening in the handle to hold the brush end and the handle assembled. U.S. Pat. No. 2,229,084 by Horne discloses a brush having a shank with an opening in the same that extends into the handle, and a spring clip, mounted on the detachable handle, has an end that extends into the opening or slot in the shank of the brush. U.S. Pat. No. 4,406,559 by Geertsema et al, discloses a tool handle and a socket wherein the tool, rather than having a boss thereon has an opening through the same into which a projection on the retaining member extends when the shank of the tool is inserted into the handle mounted socket. U.S. Pat. No. 1,894,882 by Mazzella and U.S. Pat. No. 2,810,147 by Aman disclose hair brushes with detachable bristle portions. U.S. Pat. No. 3,081,783 by Miller teaches a detachable brush having a boss extending from the shank thereof which engages a groove in a handle and may be retained therein by rotating the handle relative to the brush head. None of the foregoing prior art teach or suggest the apparatus for handling hairstyling brushes, or the method for handling hairstyling brushes, of this invention.

SUMMARY OF THE INVENTION

This invention accomplishes its desired objects by providing an apparatus for handling hairstyling brushes and which includes a pair of end walls, a back wall secured to the end walls, a bottom attached to the end walls and the back wall, and an upright support wall connected to the bottom of the back wall. A cross brace attaches to the support wall and to one of the end walls. An upper door pivotally attaches at its bottom to the cross brace, and a lower door pivotally attaches to the bottom underneath the upper door. A perforate tray is slidably positioned to the upright support wall and to one of the end walls behind the upper door. At least one primary reservoir container is situated on top of the apparatus for handling hairstyling brushes to hold a sterilizing fluid and to receive a closed shank having groups of bristles within this sterilzing fluid in order to sterilize the bristles.

This invention further accomplishes its desired objects by providing a method for handling hairstyling brushes which comprises the steps of releasing a boss means of a brush head means from within an aperture of the biasing latch means and from extending and operating through the slot of the generally cylindrical handle means. The method further comprises positioning the brush head in a sterilized fluid contained in a reservoir container of the apparatus for handling hairstyling brushes.

It is an object of this invention to provide an apparatus for handling hairstyling brushes.

Still further objects of this invention reside in the provision of a method for handling hairstyling brushes.

These together with the various ancillary objects and features as will become apparent as the following description proceeds, are attained by this invention, preferred embodiments being shown in the accompanying drawings, by way of example only, wherein:

BRIEF DESCRIPTION OF THE DRAWINGS

FIG. 1 is a perspective view of the hairstyling brush according to the invention;

FIG. 2 is a side elevational view of the hairstyling brush;

FIG. 3 is a top plan view of the hairstyling brush;

FIG. 4 is a perspective view of the generally cylindrical handle of the hairstyling brush;

FIG. 5 is a vertical sectional view taken in direction of the arrows and along the plane of line 5—5 in FIG. 2;

FIG. 8 is a front elevational view of the apparatus for handling hairstyling brushes;

FIG. 9 is a top plan view of the apparatus for handling hairstyling brushes;

FIG. 10 is an elevational view of the apparatus for handling hairstyling brushes with the upper and lower doors lowered in an open position;

FIG. 11 is a perspective view of the perforated tray;

FIG. 12 is a front perspective view of a support hanger which receives the perforated tray; and FIG. 13 is a rear perspective view of a support hanger which receives the perforate tray.

DETAILED DESCRIPTION OF THE INVENTION

Figure 6:
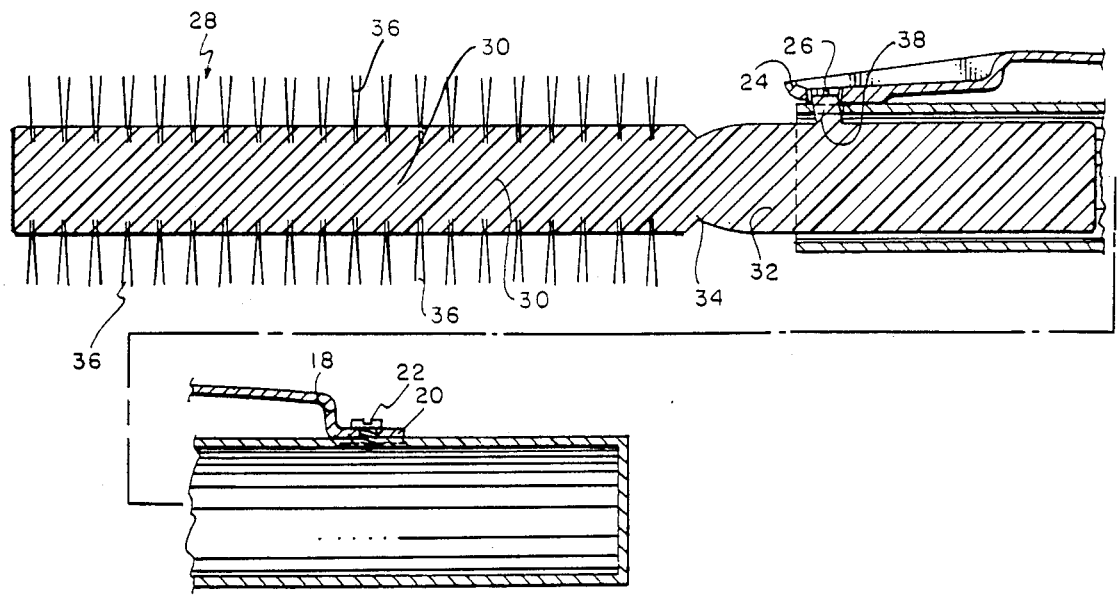
FIG. 6 is a vertical sectional view taken in, direction of the arrows and along the plane of line 6—6 in FIG. 3.
Figure 7:
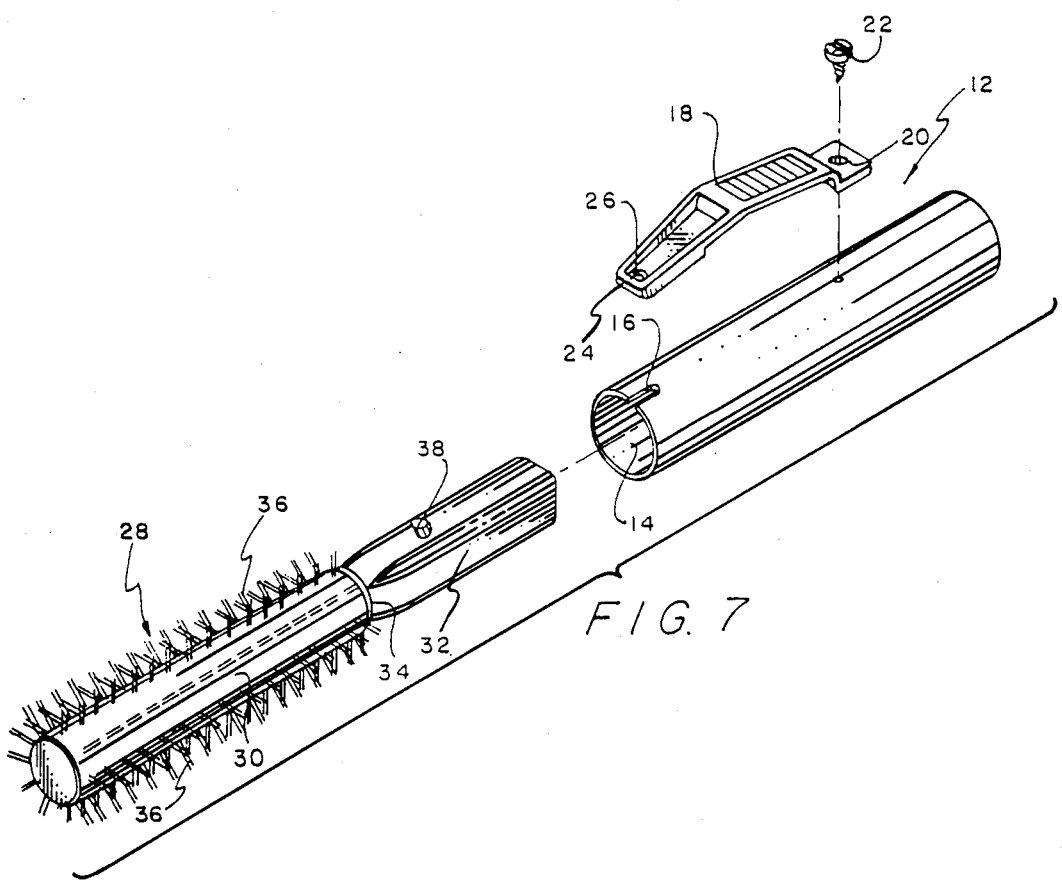
FIG. 7 is an exploded, perspective disassembled view of the hairstyling brush of this invention.

Referring now in detail to the drawings, wherein like reference numerals designate similar parts throughout the various views, there is seen a hairstyling brush, generally illustrated as 10. Brush 10 comprises a generally cylindrical handle, generally illustrated as 12 (see FIG. 4) including a structure defining a generally cylindrical reservoir 14 and a slot 16 (see FIG. 6) with an open end. The handle 12 additionally includes a biasing latch 18 having one end 20 secured to the handle 12 by bolt 22 and another end 24 having a structure defining an aperture 26 which generally registers with the slot 16.

A brush, generally illustrated as 28 has a structure defining a closed shank 30, an open shank 32, and a shank groove 34 which circumscribes the structure of the brush 28 to separate the closed shank 30 from the open shank 32. A plurality of groups of bristles 36 attach to the closed shank. A boss 38 is integrally bound to the open shank 32. As illustrated in FIGS. 1, 2, 3 and 6, the open shank 32 is slidably removably lodged within the generally cylindrical reservoir 14 such that the boss 38 extends and operates through the slot 16 while simultaneously being received within the aperture 26 of the biasing latch 18.

Continuing to refer in detail to the drawings, more particularly FIGS. 8-13, there is seen an apparatus for handling hairstyling brushes, generally illustrated as 40. The apparatus 40 comprises a pair of end walls 42-42, a back wall 44 secured to the end walls 42-42, and a bottom 46 attached to the end walls 42-42 and the back wall 40. An upright support wall 48 is connected to the bottom 46 and to the back wall 44. A cross brace 50 attaches to the support wall 48 and to one of the end walls 42. An upper door 52 pivotally attaches at its bottom to the cross brace 50, and a lower door 54 pivotally attaches also at its bottom underneath the upper door 52. A perforate tray 56 is slidably positioned to the upright support wall 48 into one of the end walls 42 behind the upper door 52 (see FIGS. 8 and 10). At least one primary reservoir container 58 (See FIG. 8) is situated on top of the apparatus 40 to hold a sterilizing fluid and to receive the closed shank 30 having the groups of bristles 36 within the sterilizing fluid in order to sterilize the bristles 36 and the closed shank 30.

The apparatus 40 additionally comprises a top 60 which is secured to the top of the support wall 48, the back wall 44, and one of the end walls 42 and has a structure defining a pair of openings 62-62 to receive a pair of the primary reservoir containers 58-58. An upright generally U-shaped partition 64 is mounted on the top 62 to enclose the pair of primary reservoir containers 58-58 and acts in a similar fashion as a splashback behind a kitchen stove. A lid 66 is pivotally attached at its back to the opposite end wall 42 which the top 60 is connected to and includes a lip 68 which registers with the top of the upright support wall 48 and a side of the U-shaped partition 64 (See FIGS. 8 and 9). Three secondary reservoir containers, 70-70-70 are positioned in three openings 72-72-72 underneath the lid 66 of the apparatus 40 for handling hairstyling brushes. A pair of channeled support hangers 74-74 (see FIGS. 12 and 13) having channels 76-76 are connected to one of the support end walls 42 and to the upright wall 48 in order that the perforate tray 56 can slidably lodge within the channels 76-76 of the pair of channeled support hangers 74-74. The three secondary containers 70-70-70 include sterilizing fluid for sterilizing scissors, combs, razors, or the like. If it is desired, one of the three secondary containers 70 may be left dry in order to store sterilized razors, scissors, and/or combs.

With continuing reference to the drawings for operations of the invention and the method for handling hairstyling brushes, the boss 38 of the brush 28 is released from within the aperture 26 of the biasing latch 18 and from extending and operating through the slot 16 of the generally cylindrical handle 12 in order to separate the brush 28 from the handle 12 in order to position the brush 28 within the sterilzing fluid contained in one of the primary reservoir containers 58. The brush 28 is released by pressing downwardly on the biasing latch 18 in proximity to the center thereof in order to disinlodge the boss 138, after being released from within the aperture 26, out of the slot 16 of the handle 12.

After the brush 28 has remained within the sterilizing fluid of one of the primary reservoir containers 58 for a perdetermined amount of time, the brush 28 is removed and placed on perforate tray 56 in order to allow to drip dry.

When the brush 28 has drip dried, the boss 38 of the brush 28 is slid into the slot 16 of the generally cylindrical handle 12; and the biasing latch 18 is biased simultaneously downwardly in proximity to the center thereof simultaneously with the sliding of the boss 38 in order to readily expose the aperture 26 to the boss 38. Subsequently, the bias on the latch 18 is released in order to lodge the boss within the aperture 26. The hairstyling brush 10 now includes a sterilized brush 28 which can be subsequently utilized for styling a person's hair. After a person has had his or her hair styled, the foregoing steps may be repeated in order to resterilize the brush 28 for the next person whose hair will be styled.

Thus, by the practice of this invention, there is provided a hairstyling brush 10 in combination with an apparatus for handling hairstyling brushes 40. The two primary containers 58-58 are capable of holding a sterilizing fluid (germicidal disinfectant) in order that the hairstyling brush 10 may be immersed therein for sterilization. The perforate tray 56 provides a means for allowing the hairstyling brush, or any other brush which a barber may use, to drip dry. Two of the three secondary containers 70-70-70 may also include sterilizing fluid in order to sterilize razors, shears, combs or any of the other utensils which a barber may use. One of the three secondary containers 70 may preferably be left dry in order to store any sterilized utensil.

While the present invention hasd been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. A method for handling hairstyling brushes comprising the steps of:
   (a) releasing an immovable boss means of a brush head means from within an aperture of a biasing latch means and from extending and operating through a slot of a generally cylindrical handle means that registers with said aperture and is open on one end, in order to separate the brush head means from the cylindrical handle means, said biasing latch means being secured at one end to the handle means and generally on the same side of said handle means that has said slot; and
   (b) positioning the brush head means in a sterilzing fluid contained in a reservoir container of a means for handling hairstyling brushes.

2. The method for handling of claim 1 additionally comprising:
   (c) sliding the boss means of the brush head means into the slot of the generally cylindrical handle means after said brush head means has been sterilized; and
   (d) biasing simultaneously to step (c) said biasing latch means downwardly in proximity to the center thereof in order to readily expose the aperture to said boss means; and
   (e) releasing the bias of step (d) from said biasing latch means in order to lodge said boss means wilthin said aperture.

3. The method for handling of claim 2 additionally comprising styling a person's hair after said releasing step (e).

4. The method for handling of claim 3 additionally comprising repeating steps (a) and (b) after completing said styling step.

5. The method of claim 1 wherein said means for handling hairstyling brushes comprises a pair of end walls, a back wall secured to said end walls, a bottom attached to said end walls and said back wall and an upright support wall connected to said bottom and to said back wall, a cross brace means attached to said support wall and to one of said end walls, an upper door pivotally attached to its bottom to said cross brace means, a lower door pivotally connected to said bottom underneath said upper door, and a perforate tray means slidably positioned to said upright support wall and to one of said end walls behind said upper door.

6. The method of claim 5 wherein said biasing latch includes a pair of sloping latch surfaces integrally meeting to define a latch apex, one of said pair of sloping latch surfaces having a structure defining a plurality of ridges, to prevent slippage of a user's thumb, or the like, while the other of said pair of sloping latch surfaces has a structure defining a latch recess for receiving a user's thumb, or the like, in order that the user may lift the latch means off and away from the boss means.

* * * * *